United States Patent
May et al.

(10) Patent No.: US 6,403,671 B1
(45) Date of Patent: Jun. 11, 2002

(54) POLYMERIZABLE COMPOSITION AND THE APPLICATION THEREOF AS A COUPLING AGENT

(75) Inventors: Robert May, Seefeld; Markus Mikulla, Andechs-Frieding; Peter Bissinger, Mering, all of (DE)

(73) Assignee: ESPE Dental AG, Seefeld (DE)

( * ) Notice: Subject to any disclaimer, the term of this patent is extended or adjusted under 35 U.S.C. 154(b) by 0 days.

(21) Appl. No.: 09/486,992

(22) PCT Filed: Nov. 6, 1998

(86) PCT No.: PCT/EP98/07092

§ 371 (c)(1),
(2), (4) Date: Mar. 6, 2000

(87) PCT Pub. No.: WO99/24477

PCT Pub. Date: May 20, 1999

(30) Foreign Application Priority Data

Nov. 7, 1997 (DE) .......................................... 197 49 349

(51) Int. Cl.$^7$ ................................................. C08F 2/46
(52) U.S. Cl. ............................ 522/77; 522/79; 522/81; 522/83; 522/167; 522/168; 522/182; 522/178; 523/115; 523/113; 523/116; 523/114; 523/118; 523/300; 433/228.1
(58) Field of Search .............................. 522/74, 77, 78, 522/79, 81, 83, 167, 168, 178, 182, 908; 523/116, 114, 115, 113, 118, 300; 433/228.1; 525/43, 410, 412

(56) References Cited

U.S. PATENT DOCUMENTS

| | | | |
|---|---|---|---|
| 4,863,993 A | | 9/1989 | Montgomery |
| 4,886,859 A | * | 12/1989 | Denzinger et al. ........ 525/327.8 |
| 5,334,625 A | * | 8/1994 | Isben et al. .................. 523/115 |
| 5,348,988 A | * | 9/1994 | Suh et al. .................... 523/118 |
| 5,401,783 A | | 3/1995 | Bowen |
| 5,658,963 A | | 8/1997 | Qian et al. |

FOREIGN PATENT DOCUMENTS

| | | |
|---|---|---|
| DE | 2635123 | 2/1977 |
| DE | 3490336 C2 | 9/1985 |
| DE | 3610808 C2 | 10/1986 |
| DE | 3632868 C2 | 10/1987 |
| DE | 4137076 C2 | 5/1993 |
| DE | 19603577 A1 | 8/1997 |
| DE | 19616984 A1 | 10/1997 |
| DE | 19652144 C1 | 1/1998 |
| EP | A20325038 | 7/1989 |
| EP | A10353899 | 2/1990 |
| WO | 97 02328 | 1/1997 |

OTHER PUBLICATIONS

Japanese Abstract: JPA3–52844A, dated Mar. 7, 1991.

* cited by examiner

*Primary Examiner*—James J. Seidleck
*Assistant Examiner*—Sanza L. McClendon
(74) *Attorney, Agent, or Firm*—Birch, Stewart, Kolasch & Birch, LLP

(57) ABSTRACT

The invention relates to a polymerizable, cross-linkable composition which contains: (A) 1–99.99 wt.-% of at least one conversion product of OH-functional (meth)acrylates with (i) oligomers from unsaturated rings or heterocyclic rings and maleic anhydride and/or with (ii) at least one ring-shaped polycarboxylic acid with at least 4 ring-carbon atoms and/or the anhydrides thereof with a saturated ring system, at least 4 carboxyl groups, and 0 or 1 heterocyclic ring atoms from the group N, O, S, whereby at least one carboxyl group and/or anhydride group of the above described substance groups is reacted with unsaturated polymerizable groups; (B) 0 to 98.99 wt.-% of one or more polymerizable, unsaturated organic compounds with at least one $CH_2=C(R_{10})$—COO-group, whereby R10 represents H or methyl; (C) 0.01 to 5 wt.-% initiators and optional activators; (D) 0 to 90 wt.-% common solvents; (E) 10 to 90 wt.-% common fillers, pigments, thixotropy auxiliary agents, softening agents, diluting agents, rigidifying monomers, free-radical scavengers, stabilizing agents, and other auxiliary agents. The given wt.-% refers to the sum of all components (A) to (E). The composition is suited for bonding, casting or coating substrates and is especially suited as dental coupling agents, dental filling materials, dental cements, or dental sealers in the fields of dentistry and dental technology.

19 Claims, No Drawings

POLYMERIZABLE COMPOSITION AND THE APPLICATION THEREOF AS A COUPLING AGENT

This application is the national phase under 35 U.S.C. §371 of PCT International Application No. PCT/EP98/07092 which has an International filing date of Nov. 6, 1998, which designated the United States of America.

The invention relates to polymerizable, cross-linkable compositions, containing polyalkylbenzene derivatives and or derivatives of ring-shaped polycarboxylic acid and/or their anhydrides as well as their use in particular in dentistry. Such compositions adhere to different, but particularly to biological, substrates. Compounds of this type can be used or added for general purposes, but particularly in dentistry as components for polymerizable adhesion promoters, adhesion filling materials, adhesion cements, sealers and for similar mixtures.

Polymerizable mixtures based on monomer compounds provided with one or more unsaturated groups form the basis for a number of plastics, with mainly compounds with acrylate and methylacrylate groups being important in the dental and medical fields. Such mixtures are e.g. the basis for plastic filling and sealing materials. These polymerizable mixtures cannot generally however form a chemical compound with other materials, particularly biological substrates, unless these substrates themselves also contain sufficiently unpolymerized polymerizable groups.

A firmer connection can thus be achieved only via retention-rich surfaces, i.e. via a bond of a purely mechanical type, e.g. after etching the surface of biological or inorganic materials. By using adhesion promoters, i.e. substrates which on the one hand can chemically react with biological or inorganic material and on the other hand also bear a polymerizable group, this shortcoming can however be overcome.

A series of such adhesion promoters is already known, e.g. the organosilane-bearing vinyl or methylacryl groups. They are however limited in their adhesion effect on silicon dioxide, silicon dioxide-containing glasses as well as ceramics and metal oxides, or base metals forming these. They show no adhesion on biological substrates and particularly on tooth- or bone substrates, but have more of a separating effect. For substrates of this type a series of polymerizable adhesion promoters with other adhesion groups have been found. There are some which react with the collagen or collagen-like content of these substrates, such as e.g.

2-N-allyamino-4,6-dichloro-1,3,5-triazine (U.S. Pat. No. 4,203,220), combinations of hydroxymethacrylester with dialdehydes (EP-A-0141324) or epoxy methacrylates Furthermore there are a number of polymerizable compounds which react with the apatite compounds of tooth- or bone substance. These adhesion-promoting compounds bear acid groups or reactive acid group derivatives. Examples of such polymerizable compounds are:

unsaturated organic esters of phosphoric- or phosphonic acids (DE-A-27 11 234, DE-A-31 50 285):

unsaturated organic esters of monofluorophosphoric acid (U.S. Pat. No. 3,997,504):

unsaturated organic esters of acids of phosphorus which contain chlorine or bromine directly bound to the phosphorus (EP-A-0 058 483);

unsaturated organic esters of phosphoric acid, which are present as cyclic pyrophosphates (anhydrides) (DE-A-30 48 410).

Polymerizable carboxylic acids and reactive carboxylic acid derivatives are also known which show adhesion to tooth substance, such as e.g.

4-methacryloyloxyethyltrimellitic acid and its anhydride (Takeyama, M. et al., J. Jap. Soc. f. Dent. App. a. Mat. 19, 179 (1978)) or methacroyloxy-ethyl-o-phthalate (E. Mashuhara, K. Kojhima, N. Tarumi, N. Nakabayashi, H. Hotta, Rep. Inst. Med. Dent. Eng. 1, 29, (1967).

Reaction products of ethylenically unsaturated alcohols with 3 to 12 C atoms with cyclic anhydrides are also used as adhesion promoters (U.S. Pat. No. 4,659,751, Bowen).

Systems based on phosphoric acid are extremely hydrolysis-sensitive and those based on carboxylic acids have the disadvantage that a bond with the substrate can not be optimally carried out. Most adhesion molecules are in addition difficult to obtain by synthesis and can thus be used economically only with difficulty. There is therefore a great interest in obtaining easily accessible adhesion molecules which are hydrolysis-stable, bond more readily to the substrate than do the molecules in the prior art and can also be produced at favourable cost and economically.

The object of the invention is to make available polymerizable and cross-linkable compositions which show a high adhesion, in particular to biological substrates and quite particularly to hard tooth substance and dentine.

Surprisingly, compositions which contain molecules which have formed from the reaction of molecules of the general formula (1) or ring-shaped polycarboxylic acids and/or their anhydrides with a saturated ring system and at least four carboxyl groups as well as 0 or 1 heterocyclic ring atoms from the group N, O, S, with OH-functional (methyl) acrylates (general formula (3)), adheres to biological substrates, in particular to hard tooth substances such as enamel and dentine, to a greater degree than previously known. By combining these molecules in an adhesion-promoting composition a further increase in adhesion is unexpectedly observed.

The invention is explained in more detail in the following.

In the following, the term (meth)acrylates is understood to refer to methacrylate acid esters, acrylic acid esters, methylacrylamides, acrylamides as well as thiomethacrylic acid esters and thioacrylic acid esters.

The polymerizable cross-linkable compositions according to the invention have to contain adhesion-promoting substances alongside other components, such as for example fillers, monomers or solvents.

The composition according to the invention consists of:
(A) 1 to 99.99 wt.-%, preferably 5 to 70 wt.-%, of reaction products of OH-functional (meth)acrylates with
(i) the compounds of formula (1):

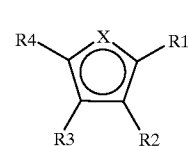

(1)

in which:
R1, R2, R3 and R4 are chosen independently from each other from the group
(a) hydrogen
(b) linear or branched hydrocarbon radicals with 1 to 20 C atoms, preferably methyl,
(c) linear or branched hetero aliphatics with 1 to 20 C atoms and heteroatoms chosen from the groups N, O, S, preferably O, (d) halogens and pseudohalogens, preferably F, Cl, Br, CN, SCN, quite particularly preferably Cl, Br and (e) the fragment of formula (2):

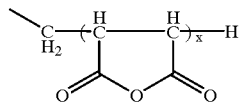

(2)

in which x can assume whole numerical values between 1 and 8,
and X is chosen from the group O, S,

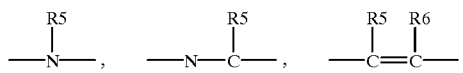

preferably

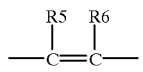

with R5 or R6 corresponding to the above definition of R1 to R4, on the condition that at least two random representatives of the group R1 to R4, R5, R6 correspond to the fragment of formula (2), the substitution pattern of the fragments of formula (2) being able to be ortho, meta or para (reaction product group A1) and the combination R1 to R4=H, X=

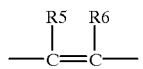

with R5=R6=fragment of formula (2) being preferred, and/or with (ii) ring-shaped polycarboxylic acids with at least 4 ring carbon atoms and/or their anhydrides with a saturated ring system and at least four carboxyl groups as well as 0 or 1 hetero ring atoms from the group N, O, S (reaction product group A2) of the general formula (3),

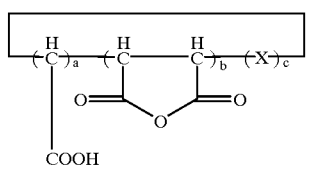

(3)

where
a=0 to 6,
b=0 to 3,
c=0 or 1, and
X=0, NR1 or S,
R1 has the above meaning, except for (e) a fragment of formula (2), and
at least one carboxyl group and/or anhydride group of the above-named substance group is functionalized with unsaturated polymerizable groups, (B) 0 to 98.99 wt.-%, preferably 5 to 70 wt.-%, of one or more polymerizable, unsaturated organic compounds with at least one $CH_2$=$C(R10)$—COO-group, where R10 is =H or methyl;

(C) 0.01 to 5 wt.-%, preferably 0.01 to 3 wt.-%, of initiators and optionally activators;

(D) 0 to 99 wt.-%, preferably 0 to 50 wt.-%, of customary solvents;

(E) 0 to 90 wt.-%, preferably 20 to 80 wt.-%, of customary fillers, pigments, thixotropy auxiliaries, plasticizers, diluting agents, rigidifying monomers, radical captors, stabilizers, other auxiliaries, the given wt.-% referring in each case to the sum of all components (A) to (E).

Preferred compounds of formula (1) correspond to following formula (4)

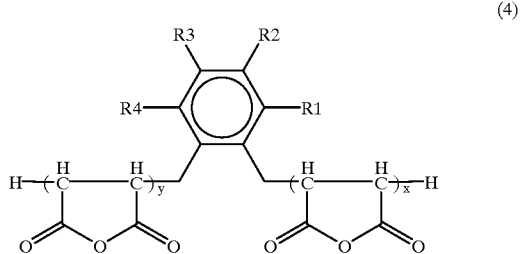

(4)

in which x and y independently of each other can assume whole numerical values between 1 and 8 and R1, R2, R3 and R4 have the above-mentioned meanings according to formula (1) (a)–(d). The corresponding compounds in which the substituents bearing the anhydride groups are arranged, not in ortho-, but in meta- or in para-position on the benzene ring are furthermore preferred.

Synthesis of compounds of the general formula (1) is known. DE-A-2 405 284 (Ciba-Geigy), EP-A-0 383 724 (Ciba-Geigy), GB-A-1 529 092 (Ciba-Geigy) and GB-A-2 164 339 describe the polymerization of maleic anhydride using a peroxide initiator in a diluted solution in o-xylene. Synthesis can be carried out by combining and heating the three original substances, xylylene compound, preferably 1,2-xylene, maleic anhydride and radical initiator, for example di-tert.-butylperoxide, tert-butylhydroperoxide, dibenzoylperoxide or α,α'-azo-isobutyronitrile. The initiator can also be added to the mixture of the other two educts. The reaction can take from a few hours to several days depending on the substances used and reaction temperature. After the reaction has finished, the product is obtained by removal of the excess xylylene component as a raw material and can be used for the next synthesis step without further purification.

The product of this first synthesis stage contains according to the general formulae (1) and (2), a structural segment, resulting from the xylylene component used, which is covalently bound via methylene groups to a single maleic anhydride fragment (MA-fragment) each or several MA-fragments covalently linked to each other. The product accordingly contains a mixture of substances of the general formulae (1) and (2) with different anhydride functionalities. When using 1,2-xylene, a product with x=4 to 6 MA fragments preferably forms. If 1,4-xylene or mesitylene is used, the number of attached MA-units x is preferably 2 to 3.

In a second synthesis step, the reaction product of the general formulae (1) and (2) is partially or completely esterified with an OH-functional (meth)acrylate, preferably 2-hydroxyethylmethacrylate (HEMA), 3-hydroxypropyl (meth)acrylate, 2-hydroxyethyl(meth)acrylamide, 2-hydroxyethylthiol(meth)acrylate or isopropylidene-bis-[2-hydroxy-3-(4-phenoxy)propyl]-methacrylate, quite particularly preferably 2-hydroxyethylmethacrylate (reaction product group A1).

To this end, the product of general formulae (1) and (2) is dissolved in an inert organic solvent, for example tetrahydrofuran (THF) and is fully reacted in the presence of an acid or base catalyst with the desired amount of OH-functional (meth)acrylate. Sulphuric acid, 4-toluenesulphonic acid, methanesulphonic acid, sodium acetate or pyridine can be used for example as catalysts. The reaction is carried out at temperatures between 20 and 70° C., preferably at 50 to 60° C. Reaction times of 1 to 7 days are necessary, depending on stoichiometry, anhydride/OH-functional (meth)acrylate, temperature and catalyst.

The anhydride/OH-functional (meth)acrylate ratio used is preferably less than one, particularly preferably 0.1 to 0.9 and quite particularly preferably 0.2 to 0.7.

The completeness of the reaction can be checked by means of thin-layer chromatography or NMR spectroscopy. If the anhydride/OH-functional (meth)acrylate stoichiometry chosen is greater than one, the anhydride remaining after the reaction can be hydrolyzed with water. This reaction can be monitored by means of IR spectroscopy.

The end-product is obtained after extraction of the preparation by means of an organic solvent, such as for example diethyl ether, methyl-tert.-butyl ether, chloroform, methylene chloride or toluene. The fragments of formula (2) have been transformed into fragments of formula (5):

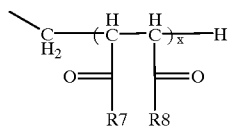

(5)

the definition of x corresponding to that in the general formula (2) and R7 and R8 independently of each other being able to be OH, OR9, with at least one representative of the group R7 and R9 having to be OR9, R9 standing for a (meth)acrylate-functionalized group, preferably an aliphatic, aromatic or araliphatic group, the aliphatic groups preferably containing 4 to 10 C atoms, for example

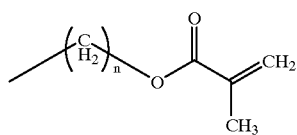

with n=1 to 7, preferably n=2 or 3 or

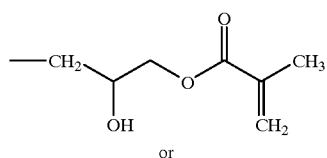

or

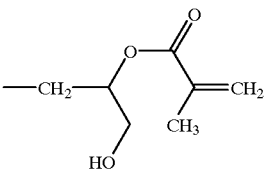

The substitution pattern of the two fragments of formulae (2) or (5) can be ortho, meta or para, preferably ortho.

Products which have resulted from an incomplete reaction of the compounds of general formulae (1) and (2) via the previously described reaction and thus contain non-converted anhydride groups, also falling within the scope of this invention.

The end-product of this reaction represents a mixture of several substances, of which each can have a different number of carboxylic acid and (meth)acrylate-functional ester groups. Accordingly, there is no uniform molecular weight; the average molecular weight of monomers [(1)+(2)] is 300 to 4000 g/mol, preferably 600 to 1000 g/mol. Additionally the compounds contained in the mixture are regioisomeric vis-à-vis each other as, during the reaction of the product of general formulae (1) and (2) with OH-functional (meth)acrylate, the OH-groups can attach themselves to different anhydride groups and given an anhydride group to two different C atoms.

The original compounds of one component of the reaction product group A2 of the claimed compositions, namely the ring-shaped polycarboxylic acids of the general formula (3) with at least 4 ring-carbon atoms with a saturated ring system as well as their anhydrides with at least 4, preferably 4 to 9, particularly preferably 4 to 7 quite particularly preferably 4 to 6 carboxyl groups as well as 0 or 1 hetero ring atoms from the group N, O, S, preferably N and O, particularly preferably O, are freely accessible.

2,3,4,5-tetrahydrofuran tetracarboxylic acid and 1,2,3,4,5,6-cyclohexane hexacarboxylic acid as well as their anhydrides are preferably used. These compounds are freely available.

The conversion into the adhesion-promoting component according to the invention (reaction product group A2) takes place by a reaction of OH-functional (meth)acrylate with the original compound in a customary solvent, for example tetrahydrofuran. 2-hydroxyethyl(meth)acrylate, 3-hydroxypropyl(meth)acrylate, 2-hydroxyethyl(meth)acrylamide, 2-hydroxyethylthiol(meth)acrylate and isopropylidene-bis-[2-hydroxy-3-(4-phenoxy)-propyl] methacrylate are preferred OH-functional (meth)acrylates. A mixture of partly esterified molecules can also result as product. In order to control the degree of esterification, appropriate anhydrides can be used which are also freely available. In the case of the dianhydride of tetrahydrofuran tetracarboxylic acid, a diester is selectively obtained, for example.

The reaction products accordingly conform to general formula (6):

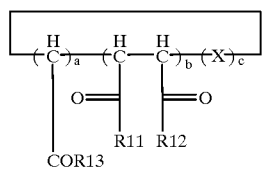

(6)

in which X, a, b and c are as defined above and $R_{11}$, $R_{12}$ and $R_{13}$ independently of each other can stand for OH or $OR_9$ provided that at least one representative of group $R_{11}$, $R_{12}$ and $R_{13}$ must be $OR_9$, $R_9$ having the above meaning. In the case where b is equal to 0, at least one carboxylic acid group must be converted.

Component (A) is present in the compositions according to the invention in an amount of 1 to 99.99 wt.-%, preferably 5 to 70 wt.-%, relative to the total weight of the composition.

Component (B) of the compositions according to the invention, a polymerizable unsaturated organic compound with at least one $CH_2=C(R10)$—COO group, where R10=H or methyl, is understood to mean a polymerizable unsaturated organic compound with an acryloyl- or methyacryloyl group. Amongst others esters of acrylic or methacrylic acid, are preferred. Examples are methyl methacrylate, methyl acrylate, ethyl methacrylate, ethyl acrylate, propyl methacrylate, propyl acrylate, isopropyl methacrylate, isopropyl acrylate, hydroxymethyl methacrylate, hydroxymethyl acrylate, hydroxyethyl methacrylate, hydroxyethyl acrylate, hydroxypropyl methacrylate, hydroxypropyl acrylate, tetrahydrofurfuryl methacrylate, tetrahydrofurfuryl acrylate, glycidyl methacrylate, glycidyl acrylate, triethylene glycol dimethacrylate, triethylene glycol diacrylate, tetraethylene glycol dimethacrylate, tetraethylene glycol diacrylate, trimethylolethane trimethacrylate, trimethylolpropane trimethacrylate, pentaerythritrol trimethacrylate, trimethylolethane triacrylate, trimethylolpropane triacrylate, pentaerythritrol triacrylate, pentaerythritrol tetramethacrylate, pentaerythritrol tetraacrylate, ethylene dimethacrylate, ethylene diacrylate, ethylene glycol dimethacrylate, ethylene glycol diacrylate, butylene glycol dimethacrylate. butylene glycol diacrylate, neopentylglycol dimethacrylate, neopentylglycol diacrylate, 1,3-butanediol dimethacrylate, 1,3-butanediol diacrylate, 1,4-butanediol dimethacrylate, 1,4-butanediol diacrylate, 1,6-hexanediol dimethacrylate, 1,6-hexanediol diacrylate, di-2-methacryloxyethyl hexamethylene dicarbamate, di-2-methacryloxyethyl trimethylhexamethylene dicarbamate, di-2-methacryloxyethyl dimethylbenzene dicarbamate, di-2-methacryloxyethyl dimethylcyclohexane dicarbamate, methylene-bis-2-methacryloxyethyl-4-cyclohexylcarbamate, di-1-methyl-2-methacryloxyethyl hexamethylene dicarbamate, di-1-methyl-2-methacryloxyethyl trimethylhexamethylene dicarbamate, di-1-methyl-2-methacryloxyethyl dimethylbenzene dicarbamate, di-1-methyl-2-methacryloxyethyl dimethylcyclohexane dicarbamate, methylene-bis-1-methyl-2-methacryloxyethyl-4-cyclohexyl carbamate, di-1-chloromethyl-2-methacryloxyethyl hexamethylene dicarbamate, di-1-chloromethyl-2-methacryloxyethyl trimethylhexamethylene dicarbamate, di-1-chloromethyl-2-methacryloxyethyl dimethylbenzene dicarbamate, di-1-chloromethyl-2-methacryloxyethyl dimethylcyclohexane dicarbamate, methylene-bis-2-methacryloxyethyl-4-cyclohexyl carbamate, di-1-methyl-2-methacryloxyethyl hexamethylene dicarbamate, di-1-methyl-2-methacryloxyethyl trimethylhexamethylene dicarbamate, di-1-methyl-2-methacryloxyethyl dimethylbenzene dicarbamate, di-1-methyl-2-methacryloxyethyl dimethylcyclohexane dicarbamate, methylene-bis-1-methyl-2-methacryloxyethyl-4-cyclohexyl carbamate, di-1-chloromethyl-2-methacryloxyethyl hexamethylene dicarbamate, di-1-chloromethyl-2-methacryloxyethyl timethylhexamethylene dicarbamate, di-1-chloromethyl-2-methacryloxyethyl dimethylbenzo dicarbamate, di-1-chloromethyl-2-methacryloxyethyl dimethylcyclohexane dicarbamate, methylene-bis-1-chloromethyl-2-methacryloxyethyl-4-cyclohexyl carbamate, 2,2'-bis(4-methacryloxyphenyl)-propane, 2,2'-bis(4-acryloxyphenyl)-propane, 2,2'-bis(4(2-hydroxy-3-methacryloxyphenyl))-propane, 2,2'-bis(4(2-hydroxy-3-acryloxyphenyl))-propane, 2,2'-bis(4-methacryloxyethoxyphenyl)-propane, 2,2'-bis(4-acryloxyethoxyphenyl)-propane, 2,2'-bis(4-ethacryloxypropoxyphenyl)-propane, 2,2'-bis(4-acryloxydiethoxyphenyl)-propane, 2,2'-bis(4-methacryloxydiethoxyphenyl)-propane, 2,2'-bis-(4-acryloxydiethoxyphenyl)-propane, 2,2'-bis(3(4-phenoxy)-2-hydroxypropane-1-methacrylate)-propane, 2,2'-bis(3(4-phenoxy)-2-hydoxypropane-1-acrylate)-propane etc.

As stated above, a number of methacrylates and acrylates can be used. These can be used alone or in combinations of two or more. It is to be pointed out that the present invention is not necessarily limited to such methacrylates and acrylates, rather that similar compounds can be used in the same way. On the other hand, the polymerizable unsaturated organic compound which contains at least one $CH_2=C(R10)$—COO group in which R10 stands for H or methyl, can be used in combination with a polymerizable organic compound, such as styrene, N-vinylpyrrolidone and divinylbenzene.

The different esters of acrylic acid and methylacrylic acid do not necessarily have to be used alone: they can also be used in combinations of two or more. In particular urethane, epoxy and polyol(meth)acrylates can account for 50% or more of the total weight of component B, i.e. the polymerizable unsaturated organic compound which contains at least one $CH_2=C(R10)$—COO group in which R10 stands for H or methyl. Urethane(meth)acrylate is a general term which is applied to acrylates or methacrylates with a urethane skeleton and includes for example carbamate compounds as previously mentioned. The poly(meth)acrylate defines an ester of a di- or polyhydric alcohol with acrylic or methacrylic acid. Epoxy(meth)acrylate is a general term which is applied to acryl- or methacrylate esters, which are obtained by reacting epoxy compounds with acrylate or methacrylate esters.

Monomeric and polymeric acrylates and methacrylates can also be used. Long-chained monomers can also be used advantageously, for example the monomers known from U.S. Pat. No. 3,066,112 based on bisphenol A and glycidyl methacrylate or their derivatives resulting from the addition of isocyanates.

Compounds of bisphenol A-diethyloxy(meth)acrylate and bisphenol A-dipropyloxy(meth)acrylate type are also suitable. Oligo-ethoxylated and oglio-propoxylated bisphenol A-diacrylic- and -dimethacrylic acid esters can also be used. Acrylic acid and methacrylic acid esters of at least bifunctional aliphatic alcohols, for example triethylene glycol-di(meth)acrylate, ethylene glycol-di(meth)-acrylate, hexanediol-di(meth)acrylate and trimethylpropane-tri(meth)-acrylate, are also well suited. The diacrylic and dimethacrylic acid esters of bis(hydroxy-methyl)-tricyclo $[5.2.1.0^{2.6}]$-decane and the diacrylic and dimethylacrylic acid esters of the compounds of bis(hydroxymethyl)-tricyclo $[5.2.1.0^{2.6}]$-decane extended with 1 to 3 ethylene oxide- and/or propylene oxide units, named in DE-C-2 816 823, are also particularly suitable.

The methylacrylic acid esters described in EP-A-0 235 826 e.g. triglycolic acid-bis[3(4)-methacryloxymethyl-8(9)-tricyclo[$5.2.1.0^{2.6}$]-decylmethylesters are also well-suited monomers.

Naturally, mixtures of monomers and/or of unsaturated polymers prepared from them can also be used.

The component (B) is present in an amount of 0 to 98.99 wt.-%, preferably 5 to 70 wt.-%, in the mixtures according to the invention.

Initiator systems which effect the radical polymerization of the monomers, e.g. photoinitiators or so-called redox systems, are suitable as initiators and activators of the component (C).

α-diketones such as camphorquinone, combined with secondary and tertiary amines, or mono- and bisacylphosphinic oxides such as 2,4,6-trimethylbenzoyl diphenylphosphinic oxide and bis-(2,6-dichlorobenzoyl)-4-n-propylphenyl phosphinic oxide, for example are suitable as photoinitiators. However, other compounds of this type, such as are described in the published European patent documents EP-A-0-073 413, EP-A-0-0 007 508, EP-A-0 047 902. EP-A-0 057 474 and EP-A-0 184 095, are also suitable.

The concentration of photoinitiators is preferably 0.01 to 3 wt.-% and in particular 0.1 to 2 wt.-% of the preparation.

Peroxide compounds together with so-called activators, for example, are suitable as redox initiator systems. Compounds such as lauroyl peroxide, benzoyl peroxide, o- as well as p-chlorobenzoyl peroxide and p-methylbenzoyl peroxide are considered in particular as organic peroxide compounds.

Tertiary aromatic amines are suitable for example as activators, such as the N,N-bis-(hydroxyalkyl)-3,5-xylidines known from U.S. Pat. No. 3,541,068, as well as the N,N-bis-(hydroxyalkyl)-3,5-di-t-butylaniline known from DE-A-2 658 530 and N,N-bis-(hydroxyalkyl)-3,4,5-trimethylanilines. The barbituric acids and barbituric acid derivatives described in DE-B-1 495 520 as well as the malonylsulphamide described in EP-A-0 059 451 are also well-suited activators. 2,6-dimethyl-4-isobutylmalonylsulphamide, 2,6-diisobutyl-4-propylmalonylsulphamide, 2,6-dibutyl-4-propylmalonylsulphamide, 2,6-dimethyl-4-ethylmalonysulphamide as well as 2,6-dioctyl-4-isobutylmalonylsulphamide are preferred malonylsulphamides. For further acceleration, polymerization is preferably carried out in the presence of heavy metal compounds and ionogenic halogen or psuedohalogen. Copper is particularly suitable as a heavy metal, the chloride ion is particularly suitable as halide. The heavy metal is more suitably used in the form of soluble organic compounds. The halide and pseudohalide ions are also used in the form of soluble salts, examples of which that may be named being the soluble aminohydrochlorides as well as quaternary ammonium chloride compounds.

Suitable redox systems are also those known from "Redox Polymerisation", G. S. Misra and U. D. N. Bajpaj, *Prog. Polym. Sci.*, 8, 61–131 (1982).

If the polymerizable compositions according to the invention contain a redox initiator system of organic peroxide and activator as (C), then the peroxide and activator are preferably present in parts of the compositions according to the invention which are physically separated from each other and which are homogenously mixed together only immediately before use. If the composition according to the invention contains organic peroxide, copper compound, halide and malonylsulphamide together as component (C), then it is particularly advisable for the organic peroxide, malonylsulphamide and the copper compound/halide combination to be present in three components physically separated from each other. For example, organic peroxide, polymerizable monomers as well as fillers can be kneaded into a paste and the other components can be kneaded into two separate pastes in the manner described above, each with a small quantity of fillers or in particular thixotropy auxiliaries, such as silanized silicic acid, and a plasticizer, for example phthalate. On the other hand the polymerizable monomers can also be present together with copper compound/halide and fillers. If the composition according to the invention is present in components physically separated from each other, component (E) can be present in each of these components.

Suitable solvents according to component (D) can be inorganic or organic. Naturally a mixture of these solvents can also be used. Preferred examples are water (inorganic solvent) and ketones or alcohols (organic solvents), for example ethanol and acetone or their mixtures. They are contained in the compositions in an amount of 0 to 90 wt.-%, preferably 0 to 50 wt.-%, relative to the total weight of the composition.

Inorganic and/or organic fillers, pigments, dyestuffs, thixotropy auxiliaries, plasticizers, diluting agents, radical captors, stabilizers and other auxiliaries can be contained in the composition as component (E).

Inorganic fillers can be for example quartz, ground glasses, non-water-soluble fluorides such as e.g. $CaF_2$ or $SrF_2$, silica gels as well as silicic acid, in particular pyrogenic silicic acid or its granules. They are contained in the compositions according to the invention in a concentration of 0 to 90 wt.-% preferably 20 to 80 wt.-% relative to the total mass of all components. For better incorporation into the polymer matrix, it can be advantageous to hydrophobize the fillers as well as optionally x-ray opaque additives. Customary hydrophobizing agents are silanes, for example trimethoxymethacryloxypropyl silane. In one version, all the inorganic fillers used are silanized, preferably with trimethoxymethacryloxypropyl silane. The amount of silane used is usually 0.5 to 10 wt.-% relative to inorganic fillers, preferably 1 to 6%, quite particularly preferably 2 to 5 wt.-% relative to organic fillers. The maximum average particle size of the inorganic fillers is preferably 15 μm, in particular 8 μm. Fillers with an average particle size of under 3 μm are quite particularly preferably used.

Ready-pigmented polymethyl methacrylate beads or other powdered organic polymerisates are also suitable as fillers. To increase the flexibility of the compositions it can also be advantageous to use soluble organic polymers. Polyvinylacetate as well as copolymers based on vinylchloride/vinylacetate, vinylchloride/vinylisobutylether and vinylacetate/maleic acid dibutylether for example are suitable. Dibutyl-, dioctyl- and dinonylphthalates for example are well-suited as additional plasticizers.

The complex fluorides of the general formula $A_nMF_m$ known from EP-O 717 977 can be used as fillers to increase the fluoride release of the mixtures according to the invention. In this, A stands for polyvalent cation, M a metal of the $3^{rd}$ to the $5^{th}$ main groups or $2^{nd}$ to $5^{th}$ sub-groups, n an integer from 1 to 3 and m an integer from 3 to 6. The preferred versions of EP-A-0 717 977 thus also expressly apply to this invention.

Radical captors and stabilizers are used preferably in quantities of 50 to 5000 ppm, particularly preferably in quantities of 200 to 1000 ppm. Preferred compounds are 4-methoxyphenol, 2-tert.-butyl-4,6-dimethyl-phenol or 2,6-di-tert.-butyl-4-methyl-phenol.

The invention is to be explained in more detail in the following by examples. However, the invention is in no way restricted to these examples.

PREPARATION EXAMPLE 1

Preparation of a Representative of (1)

50 g maleic anhydride are dissolved in 290 g 1,2-xylene and heated to boiling point. 3 g di-ter.-butylperoxide are added and the mixture stirred for a further 2.5 hours. After the mixture has cooled, the product settles as a yellow composition and is isolated by decanting.

PREPARATION EXAMPLE 2

Preparation of a Representative of (1)

20 g maleic anhydride are heated to boiling point in 116 g 1,4-xylene and reacted with 1.2 g di-tert.-butylperoxide. The preparation is kept at reflux for 6 hours and the excess solvent is then evaporated off. The product precipitates as a yellow, viscous liquid.

PREPARATION EXAMPLE 3

Preparation of a Representative of (1)

20 g maleic anhydride are heated to reflux in 132 g mesitylene. 1.2 g di-tert.-butylperoxide is added and the mixture stirred for a further 6 hours at boiling point. After the solvent is evaporated off, the product remains as a yellow, viscous liquid.

PREPARATION EXAMPLE 4

Preparation of a Representative of (A1)

10 g of the product obtained according to preparation example 1 are dissolved in 15 ml THF and reacted with 100 mg sulphuric acid. The preparation is heated to 50° C., mixed with 5 g 2-hydroxyethyl methacrylate, and stirred for two days at 50° C. The whole is then mixed with water and left to stand. The monomer (A1) is obtained as a yellow, viscous material after extraction and subsequent evaporation of the solvent.

PREPARATION EXAMPLE 5

Preparation of a Representative of (A1)

8 g of the product obtained according to preparation example 1 are dissolved in 15 ml THF and mixed with 80 mg sulphuric acid and 6.4 mg ionol. After heating to 60° C., 8.3 g HEMA are added. The preparation is kept for 4 days at the same temperature, mixed with water and extracted. After the solvent is evaporated off, the monomer (A1) is obtained as a yellow, viscous oil.

PREPARATION EXAMPLE 6

Preparation of a Representative of (A1)

15 g of the product obtained according to preparation example 1 are dissolved in 30 ml tetrahydrofuran and mixed with 0.25 g sodium acetate. The preparation is heated to 50° C. and 7.5 g 2-hydroxyethyl methacrylate are added. After stirring for two days at 50° C., water is added and stirring continues for one day. The monomer (A1) is obtained as a yellow, viscous material after extraction and evaporation of the solvent.

PREPARATION EXAMPLE 7

Preparation of a Representative of (A2)

24.8 g tetrahydrofuran-2,3,4,5-tetracarboxylic acid, 28.4 g glycidyl methacrylate (GMA), 100 ml tetrahydrofuran are heated to 70° C. accompanied by stirring. After 24 hours, the preparation is filtered and concentrated cold with exclusion of light. After evaporation of the solvent, a viscous, red-brown product is obtained.

PREPARATION EXAMPLE 8

Preparation of Representative of (A2)

20 g all-cis-cyclohexane-1,2,3,4,5,6-hexacarboxylic acid, 0.16 mol GMA, 50 ml THF are stirred for 20 hours at 65° C. The liquid is concentrated cold with exclusion of light after the precipitated solid is filtered off, a clear, viscous product being obtained.

PREPARATION EXAMPLE 9

Preparation of a Representative of (A2)

0.1 mol tetrahydrofuran-2,3,4,5-tetracarboxylic acid dianhydride, 0.2 mol 2-hydroxyethyl methacrylate, 100 ml THF are stirred for 20 hours at room temperature. The solution is concentrated cold with exclusion of light, a red-brown, clear, viscous product being subsequently obtained. The end-product forms, after the solvent is removed, as a wax-like precipitate which must be dried for 8 hours.

EXAMPLES 1 to 4

Comparison Examples 1 and 2

Polymerizable Adhesion Promoters According to the Invention

TABLE 1

| Component (weight-%) | Example 1 | Example 2 | Example 3 | Example 4 | Comparison example 1 | Comparison example 2 |
|---|---|---|---|---|---|---|
| Representatives of (A1) according to preparation example 4 | 20 | 0 | 15 | 20 | 0 | 0 |
| Representatives of (A1) according to preparation example 6 | 0 | 0 | 0 | 20 | 0 | 0 |
| Representatives of (A2) according to preparation example 7 | 0 | 20 | 15 | 0 | 0 | 0 |
| BTDA-HEMA (*) | 0 | 0 | 0 | 0 | 20 | 0 |
| HEMA-phthalate (**) | 0 | 0 | 0 | 0 | 0 | 20 |
| HEMA | 20 | 20 | 30 | 20 | 20 | 20 |
| TEGDMA | 19.5 | 19.5 | 19.5 | 14.5 | 19.5 | 19.5 |
| Bis-GMA | 20 | 20 | 20 | 15 | 20 | 20 |
| Camphorquinone | 0.3 | 0.3 | 0.3 | 0.3 | 0.3 | 0.3 |

TABLE 1-continued

| Component (weight-%) | Example 1 | Example 2 | Example 3 | Example 4 | Comparison example 1 | Comparison example 2 |
|---|---|---|---|---|---|---|
| Dimethyl-aminoethyl benzoate | 0.2 | 0.2 | 0.2 | 0.2 | 0.2 | 0.2 |
| Potassium hexafluorotitanate | 0 | 0 | 0 | 10 | 0 | 0 |
| Acetone | 20 | 0 | 0 | 20 | 20 | 20 |
| Water | 0 | 20 | 0 | 0 | 0 | 0 |

(*) BTDA-HEMA is a reaction product of 3,3'-3,3'-benzophenone-tetracarboxylic acid dianhydride with double the quantity of 2-hydroxyethyl methacrylate (cf. US-A-4 659 751).
(**) HEMA-phthalate is the reaction product of phthalicanhydride with 2-hydroxyethyl methacrylate (E. Mashuhara, K. Kojhima, N. Tarumi, N. Nakabayashi, H. Hotta, Rep. Inst. Med. Dent. Eng. 1, 29 (1967).

The adhesion bond was checked by means of an adhesion pull-off test on bovine teeth. Per test, 5 freshly extracted bovine teeth were ground down with sandpaper until a sufficiently large dentine surface was exposed. Wax plates with a 4-mm punched-out hole were glued onto each of these surfaces to obtain a standardized adhesion surface. For further standardization, all the testpieces obtained in this manner were etched for 15 seconds by means of a conventional phosphoric acid solution (Ätzgel Minitip, ESPE Dental-Medizin, Seefeld) according to the procedure customary in practice ("all-etch technique"). The adhesion promoters according to examples 1 to 4 and comparison examples 1 and 2 were applied to the dentine surfaces prepared in this way, and polymerized by means of a light polymerization apparatus (Elipar, ESPE). A dental composite (Pertac, ESPE) was then introduced into the recesses of the wax plates and fully polymerized. After 24 hours' storage at 36° C. and 100% air humidity, the wax plates were removed and the composite testpiece pulled off in a tensile test (Zwick universal testing machine).

The following table (2) summarizes the average values of the obtained adhesive strength in Mpa.

For the comparison with adhesion promoters from the state of the art, table (2) contains adhesion values also obtained with these adhesion promoters according to the above test procedure, the composite recommended by the manufacturer in question being used instead of the Pertac composite.

TABLE 2

| Adhesion promoter | Adhesive strength in MPa |
|---|---|
| Example 1 | 6.0 |
| Example 2 | 6.1 |
| Example 3 | 8.9 |
| Example 4 | 7.8 |
| Comparison example 1 | 2.6 |
| Comparison example 2 | 0.8 |
| Syntac SC, Vivadent | 2.1 |
| Prime & Bond, Dentsply | 3.8 |

This table shows clearly the superiority of the compositions according to the invention both compared with the use of known adhesion molecules (comparison examples 1 and 2) and compared with the use of commercially available adhesive systems (Syntac SC or Prime & Bond).

The values given for adhesion are to be regarded as relative values and not as absolute values, as when the results of several test series of the identical experiments are compared, although the relations are the same, the determined values can differ from each other when the test series are compared with each other. Because of the varying quality of the extracted teeth used, more cohesive breaks are observed in some cases.

What is claimed is:
1. Polymerizable, cross-linkable composition, characterized in that it contains
(A) 1–99.99 wt.-% of at least one reaction product of OH-functional (meth)acrylates with
(i) the compounds of formula (1):

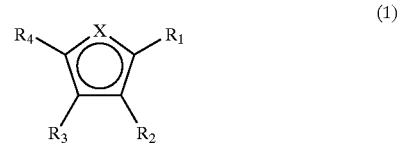

in which:
$R_1$, $R_2$, $R_3$ and $R_4$ are selected independently from each other from the group:
(a) hydrogen,
(b) linear or branched hydrocarbon radicals with 1–20 C atoms,
(c) linear or branched heteroaliphatics with 1 to 20 C atoms and heteroatoms selected from the group N, O, S,
(d) halogens and pseudo halogens, preferably F, Cl, Br, CN, SCN, and
(e) the fragment of formula (2):

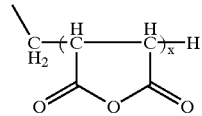

in which x can assume whole numerical values between 1 and 8, and x is selected from the group O, S,

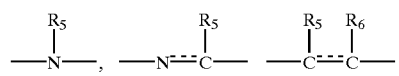

with $R_5$ or $R_6$ corresponding to the above definition of $R_1$ to $R_4$,
on the condition that at least two random representatives of the group $R_1$ to $R_4$, $R_5$, $R_6$ correspond to the fragment of formula (2), the substitution pattern of the fragments of formula (2) being able to be ortho, meta or para, and/or with (ii) at least one ring-shaped polycarboxylic acid with at least 4 ring carbon atoms and/or their anhydrides with a saturated ring system and at least four carboxyl groups as well as 0 to 1 hetero ring atoms from the group N, O, S of the general formula (3):

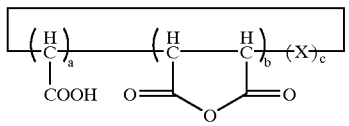

(3)

where
a=0 to 6,
b=0 to 3,
c=0 or 1, and
X=0 NR$_1$ or S,
R$_1$ having the above meaning, except for (e) a fragment of the formula (2), and
at least one carboxyl group and/or anhydride group of the above-named substance groups being reacted with unsaturated polymerizable groups
(B) 0 to 98.99 weight-% of one or more polymerizable, unsaturated organic compounds with at least one CH$_2$=C(R$_{10}$)—COO group, where R$_{10}$=H or is methyl
(C) 0.01 to 5 weight-% initiators and optionally activators
(D) 0 to 90 weight-% customary solvents
(E) 10 to 90 weight-% of fillers, pigments, thixotropy auxiliary agents, plasticizers, diluting agents, rigidifying monomers, radical captors, stabilizers, and/or other auxiliaries,
the given weight-% referring in each case go the sum of all the components (A) to (E).

2. Polymerizable, cross-linkable composition according to claim 1, characterized in that it contains as component (A) a reaction product of OH-functional (meth)acrylates with compounds of formula (4):

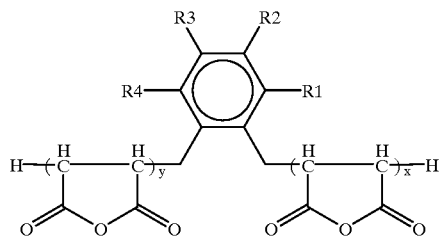

(4)

in which x and y, independently of each other, can assume whole numerical values between 1 and 8, and R1, R2, R3 and R4 have the meanings (a) to (d) specified in claim 1.

3. Polymerizable, cross-linkable composition according to claim 1, characterized in that it contains as component (A) the reaction product of compounds of formula (1), which have formed by the reaction of 1,2-xylene with maleic anhydride, with OH-functional (meth)acrylates.

4. Polymerizable, cross-linkable composition according to claim 1, characterized in that it contains as component (A) the reaction product of compounds of formula (1), which have formed by the reaction of 1,4-xylene with maleic anhydride, with OH-functional (meth)acrylates.

5. Polymerizable, cross-linkable composition according to claim 1, characterized in that it contains as component (A) the reaction product of compounds of formula (1), which have formed by the reaction of mesitylene with maleic anhydride, with OH-functional (meth)acrylates.

6. Polymerizable, cross-linkable composition according to claim 1, characterized in that it contains as component (A) compounds which have formed by the reaction of tetrahydrofuran-2,3,4,5-tetracarboxylic acid with OH-functional (meth)acrylates.

7. Polymerizable, cross-linkable composition according to claim 1, characterized in that it contains as component (A) compounds, which have formed by the reaction of tetrahydrofuran-2,3,4,5-tetracarboxylic-dianhydride with OH-functional (meth)acrylates.

8. Polymerizable, cross-linkable composition according to claim 1, characterized in that it contains as component (A) compounds, which have formed by the reaction of all-cis-cyclohexane hexacarboxylic acid with OH-functional (meth)acrylates.

9. Polymerizable, cross-linkable composition according to one of claims 3 to 8, characterized in that it contains as component (A) the reaction product with isopropylidene-bis-[2-hydroxy-3-(4-phenoxy)-propyl]methacrylate or 2-hydroxyethyl methacrylate as OH-functional (meth) acrylate.

10. A method of bonding a dental substrate comprising, adhering the composition of claim 1 to a dental substrate.

11. A method of filling a dental substrate comprising, adhering the composition of claim 1 to a dental substrate.

12. The composition of claim 1 wherein feature (E) is a member selected from the group consisting of organic fillers, inorganic fillers, pigments, thixotropy auxiliary agents, plasticizers, diluting agents, rigidifying monomers, radical captors and/or stabilizers.

13. The composition of claim 12 wherein the inorganic fillers are selected from a group consisting of quartz, ground glasses, non-water soluble fluorides and silica gels.

14. The composition of claim 13 wherein the inorganic filler particle size is 8 μm.

15. The composition of claim 13 wherein the inorganic filler particle size is 3 μm.

16. The composition of claim 12 wherein the organic fillers are selected from a group consisting of polymethyl methacrylate, polyvinylacetate, vinylchloride/vinylacetate copolymer, vinylchloride/vinylisobutylether copolymer and vinylacetate/maleic acid dibutylether copolymer.

17. The composition of claim 1 wherein the plasticizers are selected from the group consisting of dibutyl-, dioctyl-, and dinonylphthalates.

18. The composition of claim 1 wherein the filler is a complex fluoride.

19. The composition of claim 1 wherein the radical captors and stabilizers are selected from the group consisting of 4-methoxyphenol, 2-tert.-butyl-4,6-dimethyl-phenol and 2,6-ditert.-butyl-4-mehtyl-phenol.

* * * * *